United States Patent [19]

Lee et al.

[11] Patent Number: 4,544,543

[45] Date of Patent: Oct. 1, 1985

[54] PURIFICATION OF ALKYLATED ANTHRAQUINONES

[75] Inventors: Nathan D. Lee, Lambertville; Dalbir S. Sethi, Cranbury, both of N.J.

[73] Assignee: FMC Corporation, Philadelphia, Pa.

[21] Appl. No.: 488,576

[22] Filed: Apr. 25, 1983

[51] Int. Cl.$^4$ .................... C01B 15/023; C07C 50/18
[52] U.S. Cl. .................................. 423/588; 423/589; 423/590; 260/369
[58] Field of Search ............... 260/369; 423/588, 589, 423/560

[56] References Cited

U.S. PATENT DOCUMENTS

| | | | |
|---|---|---|---|
| 2,842,563 | 7/1958 | Hinegardner et al. | 260/369 |
| 2,860,036 | 11/1958 | Lait | 260/369 |
| 2,901,491 | 8/1959 | Eller et al. | 260/369 |
| 3,041,143 | 6/1962 | Dawsey | 260/369 |
| 3,132,001 | 5/1964 | Denaeyer et al. | 260/369 |
| 3,295,928 | 1/1967 | Howe et al. | 260/369 |
| 3,767,779 | 10/1973 | Coingt | 260/369 |
| 3,965,251 | 6/1976 | Shin et al. | 260/369 |

*Primary Examiner*—Glennon H. Hollrah
*Assistant Examiner*—Raymond Covington
*Attorney, Agent, or Firm*—Richard E. Elden; Eugene G. Horsky

[57] ABSTRACT

The invention is for a process for removing unalkylated anthraquinones from alkylated anthraquinone by forming a solution thereof, reducing the solution sufficiently so that at least part of the unalkylated anthraquinone is in the reduced form, and extracting the reduced solution in the absence of an oxidizing agent with an aqueous alkaline solution. The process is especially suited for removing anthraquinone from an alkylated anthraquinone for use in the manufacture of hydrogen peroxide by reducing and oxidizing a solution of the alkylated anthraquinone.

24 Claims, No Drawings

PURIFICATION OF ALKYLATED ANTHRAQUINONES

This invention relates to a process for purifying an alkylated anthraquinone.

It is well known that a commercial alkylated anthraquinone will contain impurities which may include: anthraquinone, o-benzoylbenzoic acid, and related compounds. The presence of such impurities is undesirable, particularly when the alkylated anthraquinone is to be used to manufacture hydrogen peroxide by the reduction and oxidation of a working solution comprising an alkylated anthraquinone.

In U.S. Pat. No. 2,842,563, Hinegardner et al recognize the problem caused by anthraquinone as an impurity in commercial t-butylanthraquinone when the latter is used as the working compound for the production of hydrogen peroxide. Hinegardner et al teach that an alkylated anthraquinone can be further purified when dissolved in a nonpolar solvent after a preliminary treatment with activated alumina by adding a polar solvent, such as alcohol, to supersaturate the solution with respect to anthraquinone; the supersaturated solution is then seeded with anthraquinone, and after standing from four hours to four days, the crystallized anthraquinone is separated from the solution. The process of Hinegarden et al has the disadvantage in that it is incapable of completely removing the anthraquinone from the solution. In addition, the added polar solvent must be removed from the solution requiring at least one additional step.

The process of the present invention can remove an unalkylated anthraquinone from a solution of an alkylated anthraquinone in an inert solvent or mixture of solvents. The process comprises reducing the solution containing the impure alkylated anthraquinone sufficiently to convert at least part of the unalkylated anthraquinone to the reduced form. The reduced unalkylated anthraquinone is extracted from the solution by contacting the reduced solution, in the absence of oxygen, with an alkaline, aqueous solution.

Any inert solvent for either the alkylated anthraquinone or anthrahydroquinone may be used in the process. For example, if it is more economical to remove part of the anthrahydroquinone by a physical separation process, such as filtration prior to caustic extraction, it is desirable to use an aromatic solvent for the process to ensure that substantially all of the alkylated anthraquinone is in solution prior to the reduction step. On the other hand, it may be more convenient to merely form a slurry of the alkylated anthraquinone in a polar solvent to ensure that substantially all of the anthrahydroquinone formed is in solution prior to the extraction step. Conventionally, in such a purification process it is desirable to select a solvent or solvent mixture so that no solid phase is present during the process.

If the purified alkylated anthraquinone is to be used as a solution in a process to produce hydrogen peroxide, it is preferable for the solvent in the present process to be a solvent, or a mixture of solvents, used in said hydrogen peroxide process. If desired, the purified alkylated anthraquinone may be subsequently separated from the solvent by a conventional separation process.

This invention is based on the observation that an unalkylated anthraquinone is more easily reduced than an alkylated anthraquinone. If it is desirable to merely reduce the ratio of unalkylated anthraquinone to alkylated anthraquinone, then it is necessary to reduce only part of the unalkylated anthraquinone in the solution. Generally, it is preferable to remove substantially all of the unalkylated anthraquinone when the alkylated anthraquinone is to be used to produce hydrogen peroxide.

Any suitable means for reducing the unalkylated anthraquinone may be used for the present process. The desirable reducing agents include: hydrogen in the presence of a catalyst, such as nickel or palladium either as a fixed bed or a fluid bed, sodium dithionate or any other dithionate salt, or the reduced form (anthrahydroquinone) of an alkylated anthraquinone. One skilled in the art will recognize that the present process will remove other impurities which can be either reduced and extracted from the solution or extracted from the solvent by the alkaline aqueous solution. For example, o-benzoylbenzoic acid and its alkalylated derivatives, which are intermediaries in the synthesis of the respective anthraquinones, would be extracted by the alkaline aqueous solution.

Any alkali capable of forming a water soluble salt with an anthrahydroquinone is satisfactory for the present process; sodium hydroxide and potassium hydroxide are preferred.

For the purpose of this invention, the term "alkylated anthraquinone" includes both the alkylated anthraquinone, its tetrahydro derivative, and the isomers of both, if any. For example, 2-amylanthraquinone includes the various primary, secondary, and tertiary amyl isomers of the anthraquinone and the tetrahydroanthraquinone. The specific alkylated anthraquinone selected for a commercial hydrogen peroxide process will depend on plant design factors well known to those skilled in the art. The preferred alkylated anthraquinone usually is one or more of the compounds selected from the group consisting of 2-ethylanthraquinone, 2-butylanthraquinone, and 2-amylanthraquinone, the isomers thereof, and the corresponding tetrahydroanthraquinones.

The best mode of practicing the present invention will be evident to one skilled in the art from the following non-limiting example:

EXAMPLE 1

A solution was prepared by dissolving 1600 g of a commercial 2-amylanthraquinone (contained in 3100 g of a C9-C10 aromatic solvent). The solution was hydrogenated at 43° C. at a pressure of about 250 kPa until the hydrogen taken up by the solution was equivalent to the amount of the anthraquinone originally present in the 2-amylanthraquinone. The hydrogenated solution was maintained in an inert atmosphere of nitrogen while it was ultimately contacted three successive times with 500 ml portions of a 10% aqueous solution of sodium hydroxide; after the final separation from the sodium hydroxide, the solution was then thoroughly washed with water. After the solution was separated from the washwater, the solvent was removed by distillation to permit analysis of the dissolved alkylated anthraquinone. The residue after distillation assayed over 99% amylanthraquinone; the anthraquinone content was found to be reduced from about 2% to less than 0.1%.

Pursuant to the requirements of the patent statutes, the principle of this invention has been explained and exemplified in a manner so that it can be readily practiced by those skilled in the art, such exemplification including what is considered to represent the best embodiment of the invention. However, it should be clearly understood that, with the scope of the appended claims, the invention may be practiced by those skilled in the art, and having the benefit of this disclosure, otherwise than as specifically described and exemplified herein.

What is claimed is:

1. The process for purifying a nonaqueous solution of an impure alkylated anthraquinone containing an unalkylated anthraquinone as an impurity comprising reducing said solution sufficiently to convert at least part of the unalkylated anthraquinone to a reduced form and contacting said solution in the absence of oxygen with an alkaline, aqueous solution whereby reduced unalkylated anthraquinone is extracted from the nonaqueous solution.

2. The process of claim 1 wherein the nonaqueous solution of an unalkylated anthraquinone is reduced by hydrogenating said solution in the presence of a catalyst.

3. The process of claim 1 wherein the nonaqueous solution is reduced by adding an alkylated anthrahydroquinone thereto.

4. The process of claim 1 wherein the nonaqueous solution is reduced by adding a dithionate salt thereto.

5. The process of claim 1 wherein the alkaline, aqueous solution is a solution of an alkali hydroxide selected from the group consisting of sodium hydroxide, potassium hydroxide, and mixtures of the two.

6. The process of claim 1 wherein the alkylated anthraquinone is selected from the group consisting of 2-ethylanthraquinone, 2-butylanthraquinone, 2-amylanthraquinone, tetrahydro derivatives, isomers, and mixtures thereof.

7. The process of claim 6 wherein substantially all of the unalkylated anthraquinone is converted to the reduced form.

8. The process of claim 7 wherein the alkaline, aqueous solution is a solution of an alkali hydroxide selected from the group consisting of sodium hydroxide, potassium hydroxide, and mixtures of the two.

9. The process of claim 8 wherein the nonaqueous solution of an unalkylated anthraquinone is reduced by hydrogenating said solution in the presence of a catalyst.

10. A process for purifying an impure alkylated anthraquinone containing an unalkylated anthraquinone comprising dissolving the impure alkylated anthraquinone in an inert solvent or mixture of solvents to form a solution thereof, reducing said solution sufficiently to convert at least part of the unalkylated anthraquinone to the reduced form, and contacting said reduced solution in the absence of oxygen with an alkaline, aqueous solution selected from the group consisting of sodium hydroxide and potassium hydroxide whereby unalkylated anthrahydroquinone is extracted from the solution of alkylated anthraquinone.

11. The process of claim 10 wherein substantially all of the unalkylated anthraquinone is converted to the reduced form.

12. The process of claim 10 wherein the purified alkylated anthraquinone is separated from the solvent or mixture of solvents.

13. The process of claim 12 wherein alkylated anthraquinone is selected from the group consisting of 2-ethylanthraquinone, 2-butylanthraquinone, 2-amylanthraquinone, tetrahydro derivatives, isomers, and mixtures thereof.

14. In the process for manufacturing hydrogen peroxide by the reduction and oxidation of a working solution containing an alkylated anthraquinone in a solvent or mixture of solvents, the improvement which comprises purifying the alkylated anthraquinone by dissolving said alkylated anthraquinone in a solvent to form a solution thereof, reducing said solution sufficiently to convert at least part of the unalkylated anthraquinone to the reduced form, and contacting said reduced solution in the absence of oxygen with an alkaline, aqueous solution whereby the reduced unalkylated anthraquinone is extracted from the solution of alkylated anthraquinone.

15. The process of claim 14 wherein the solution of the alkylated anthraquinone is reduced by hydrogenating said solution in the presence of a catalyst.

16. The process of claim 14 wherein the solution of the alkylated solution is reduced by adding a reduced alkylated anthraquinone to said solution.

17. The process of claim 14 wherein the solution of the alkylated solution is reduced by adding a dithionate salt to said solution.

18. The process of claim 14 wherein the alkaline aqueous solution is a solution of an alkali selected from the group consisting of sodium hydroxide, potassium hydroxide, and mixtures of the two.

19. The process of claim 14 wherein the alkylated anthraquinone is selected from the group consisting of 2-ethyanthraquinone, 2-butylanthraquinone and 2-amylanthraquinone and mixtures thereof.

20. The process of claim 19 wherein the alkali aqueous solution is a solution of an alkali hydroxide selected from the group consisting of sodium hydroxide, potassium hydroxide and mixtures of the two.

21. The process of claim 20 wherein the nonaqueous solution of an unalkylated anthraquinone is reduced by hydrogenating said solution in the presence of a catalyst.

22. The process of claim 20 wherein the nonaqueous solution is reduced by adding an alkylated anthrahydroquinone thereto.

23. The process of claim 22 wherein substantially all of the unalkylated anthraquinone is converted to the reduced form.

24. The process of claim 14 wherein substantially all of the unalkylated anthraquinone is converted to the reduced form.

* * * * *